(12) United States Patent
Pettinato et al.

(10) Patent No.: US 10,582,899 B2
(45) Date of Patent: Mar. 10, 2020

(54) IMAGING SYSTEM SUBJECT SUPPORT (71) Applicant: KONINKLIJKE PHILIPS N.V., Eindhoven (NL)

(72) Inventors: Jeremy David Pettinato, Mentor, OH (US); Shufang Dong, Mayfield Heights, OH (US); Sriram Rajagopal, Mayfield Heights, OH (US); Joanne Marie Stack Oyen, Chesterland, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 15/667,657

(22) Filed: Aug. 3, 2017

(65) Prior Publication Data
US 2017/0325754 A1   Nov. 16, 2017

Related U.S. Application Data (63) Continuation of application No. 14/390,037, filed as application No. PCT/IB2013/052786 on Apr. 8, 2013, now Pat. No. 9,750,468.

(60) Provisional application No. 61/622,104, filed on Apr. 10, 2012.

(51) Int. Cl.
| A61B 6/04 | (2006.01) |
| A61B 6/03 | (2006.01) |
| A61B 6/00 | (2006.01) |
| A61B 5/055 | (2006.01) |

(52) U.S. Cl.
CPC ............ *A61B 6/035* (2013.01); *A61B 6/0407* (2013.01); *A61B 6/0457* (2013.01); *A61B 6/4441* (2013.01); *A61B 6/4447* (2013.01); *A61B 6/503* (2013.01); *A61B 5/0555* (2013.01); *A61B 6/032* (2013.01)

(58) Field of Classification Search
CPC ..... A61B 6/035; A61B 6/0407; A61B 6/0457; A61B 6/4441; A61B 6/4447; A61B 6/503; A61B 5/0555; A61B 6/032
USPC ........................................... 378/20, 208, 209
See application file for complete search history.

(56) References Cited

U.S. PATENT DOCUMENTS

| 4,984,774 A | 1/1991 | Zupancic |
| 7,677,802 B2 | 3/2010 | Haras |
| 9,113,804 B2 | 8/2015 | Kimishima |
| 2002/0180397 A1 | 12/2002 | Henley |

(Continued)

FOREIGN PATENT DOCUMENTS

| JP | 2000014660 | 1/2000 |
| JP | 2007167408 | 7/2007 |

*Primary Examiner* — Courtney D Thomas (57) ABSTRACT

An imaging system (100) includes a gantry (101) that defines an examination region (106) and a subject support (112). The subject support includes a tabletop (116) that supports an object or subject in the examination region for a scan of the object or subject and a base (114) that supports the tabletop. A support frame (132) supports the base. The base is moveably affixed to the support frame and moves between a plurality of predetermined locations, which are based on corresponding distances from the gantry. A support frame drive system (134) moves the base alternatively to one of the plurality of predetermined locations in response to an input signal indicative of the one of the plurality of predetermined locations, which corresponds to a location of interest for the scan of the object or subject.

19 Claims, 7 Drawing Sheets

(56) References Cited

U.S. PATENT DOCUMENTS

| | | |
|---|---|---|
| 2005/0256390 A1 | 11/2005 | Laux |
| 2007/0053503 A1 | 3/2007 | Zelnik |
| 2008/0173218 A1 | 7/2008 | Wang |
| 2011/0069810 A1 | 3/2011 | Kondo |
| 2014/0033433 A1* | 2/2014 | Kimishima .......... A61B 6/0407 5/601 |

* cited by examiner

IMAGING SYSTEM SUBJECT SUPPORT

This application is a continuing application of U.S. application Ser. No. 14/390,037, which is a national filing of PCT application Serial No. PCT/IB2013/052786, filed Apr. 8, 2013, published as WO 2013/153498 on Oct. 17, 2013, which claims the benefit of U.S. provisional application Ser. No. 61/622,104 filed Apr. 10, 2012, which is incorporated herein by reference.

The following generally relates to an imaging system subject support and is described with particular application to computed tomography (CT). However, the following is also amenable to subject supports for other imaging modalities, including, but not limited to magnetic resonance imaging (MRI), positron emission tomography (PET), single photon emission tomography (SPECT), X-ray, and/or other imaging modalities.

A CT scanner includes a rotating gantry rotatably supported by a stationary gantry. The rotating gantry supports an x-ray tube, which emits radiation that traverses an examination region and a subject therein, and a detector array that detects radiation traversing the examination region and generates projection data indicative of the detected radiation. A subject support supports the subject in the examination region before, during and/or after scanning, for example, for loading the object or subject, feeding the subject into and removing the subject from the examination region, and unloading the object or subject. A reconstructor reconstructs the projection data and generates volumetric image data indicative of the portion of the subject in the examination region.

The subject support has included a base, which is fixed to the floor of the examination room and configured to move vertically, under electronic control, with respect to the floor. The subject support also includes a tabletop, which is moveably affixed to the base and configured to translate horizontally, under electronic or manual control, with respect to the base, into the examination region, cantilevering over the base, and out of the examination region for scanning Generally, the distance the base is mounted away from the stationary gantry has been based on the primary use of the scanner. For example, at a trauma center, the base is mounted at a distance so that a device such as a C-Arm scanner or other trauma device fits between the stationary gantry and the subject support, medical personnel can readily maneuver a patient immobilized on a backboard, etc.

In general imaging centers and hospitals, the base is mounted closer to the stationary gantry so as to provide at least a minimum scan length (which is the minimum distance the tabletop can travel through the examination region), for example, for a full body scan, while providing enough space between the stationary gantry and the subject support so that medical personnel can access the region between the stationary gantry and the subject support and pull the sheet the patient is lying on to move the patient towards the examination region. At a cardiac center, the base is mounted even closer to the stationary gantry. This is often done in order to reduce the amount of bounce and deflection and increase stiffness of the cantilevering tabletop, which cantilevers over the base, for cardiac scans where tabletop bounce and deflection and lack of stiffness may result in the introduction of artifact into the resulting images and thus reduce image quality.

Unfortunately, mounting the base of the subject support for any one of the types of scans, e.g., trauma scans, leaves the scanner not well-suited for the other types of scans, e.g., general and cardiac scans, and vice versa. As a consequence, for example, where an attending physician for a trauma patient orders a full body or cardiac scan, the trauma patient has to be transported to a different imaging examination room or a different facility for the full body and cardiac scans, or, one or more of the full body or cardiac scan may not be ordered or cancelled, for example, due to the patient's physiological state, time, etc. In another instance, the trauma scanner, when not being used for trauma patients, sits idle instead of being used for other billable imaging procedures, such as full body and cardiac scans, which is sub-optimal use of the scanner. In yet another instance, general and cardiac centers may be overloaded with ordered general and cardiac scans such that patients are waiting, with an available trauma scanner unable to be used to reduce or mitigate the overload.

Aspects described herein address the above-referenced problems and others.

In one aspect, an imaging system includes a gantry that defines an examination region and a subject support. The subject support includes a tabletop that supports an object or subject in the examination region for a scan of the object or subject and a base that supports the tabletop. A support frame supports the base. The base is moveably affixed to the support frame and moves between a plurality of predetermined locations, which are based on corresponding distances from the gantry. A support frame drive system moves the base alternatively to one of the plurality of predetermined locations in response to an input signal indicative of the one of the plurality of predetermined locations, which corresponds to a location of interest for the scan of the object or subject.

In another aspect, a method includes moving, via electronic control, a base of a subject support of an imaging system in a support frame with respect to a gantry of the imaging system alternatively to a first of a plurality of predetermined locations in response to a signal indicative of the first of the plurality of predetermined locations, which corresponds to a first distance of interest between the gantry and the base at which to perform a first scan of an object or subject supported by a tabletop of the subject support.

In another aspect, a computer readable storage medium is encoded with computer readable instructions. The instructions, when executed by a processer, cause the processor to: move a base (114) of a subject support (112) of an imaging system (100) between at least two different predetermined locations with respect to a gantry (101) of the imaging system to place the subject support at a location to scan an object or subject based on a type of the scan.

The invention may take form in various components and arrangements of components, and in various steps and arrangements of steps. The drawings are only for purposes of illustrating the preferred embodiments and are not to be construed as limiting the invention.

Figure 1:
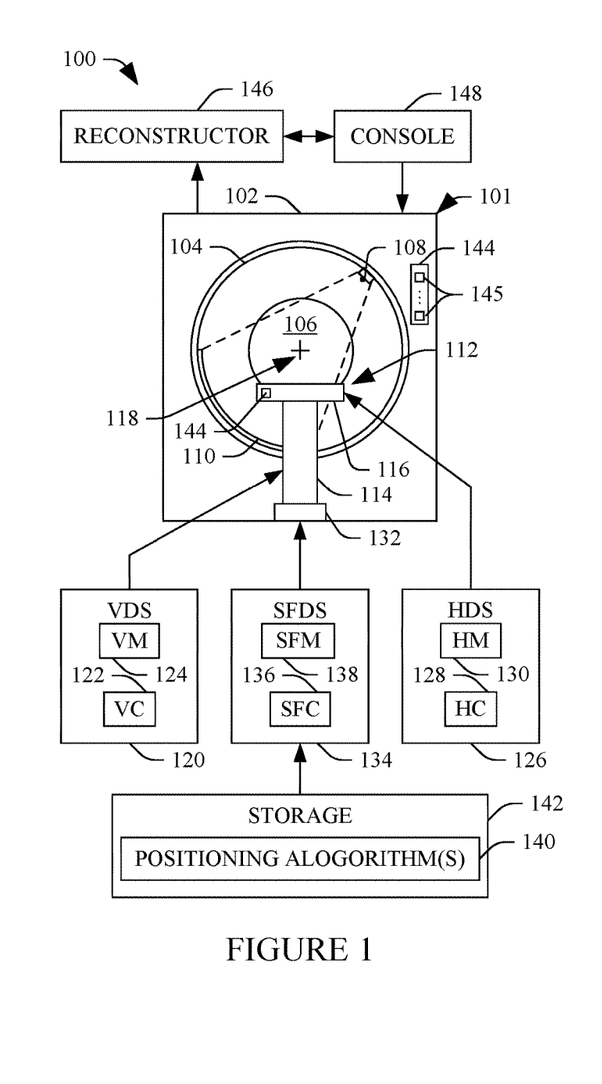
FIG. 1 schematically illustrates a front view looking into an imaging system in which a base of a subject support moves horizontally between at least two different predetermined locations within a support frame for scanning purposes.
Figure 2:
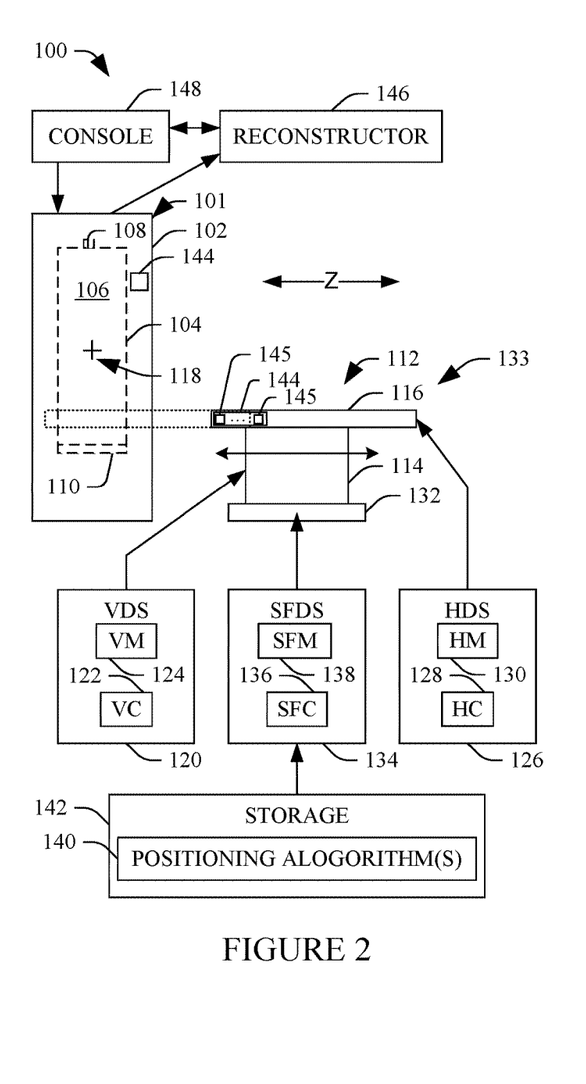
FIG. 2 schematically illustrates a side view of the imaging system of FIG. 1.

FIGS. 1 and 2 schematically illustrate an imaging system 100. The imaging system 100 can be a CT, PET, SPECT, MR, hybrid (e.g., CT/PET, etc.), X-ray, and/or other imaging apparatus. For sake of brevity and clarity, however, the following is described in connection with a CT scanner. FIG. 1 shows a front view of the scanner looking into the scanner along the z-axis, and FIG. 2 shows a side view of the scanner.

The imaging system 100 includes a gantry 101 with a stationary gantry 102 and a rotating gantry 104, which is rotatably supported by the stationary gantry 102. The rotating gantry 104 includes an aperture or examination region 106 and rotates around the examination region 106 about a longitudinal or z-axis. As such, the gantry 101 can be considered as defining the examination region 106.

A radiation source 108, such as an x-ray tube, is supported by and rotates with the rotating gantry 104 around the examination region 106. The radiation source 108 emits radiation that is collimated by a source collimator to produce a fan, wedge, cone, or otherwise shaped radiation beam that traverses the examination region 106. A radiation sensitive detector array 110 includes a one or two dimensional array of detector pixels that respectively detect radiation that traverses the examination region 106 and generates a signal indicative thereof.

A subject support 112, such as a patient couch, supports an object or subject in the examination region 106. The subject support 112 includes a base 114, which is configured to move vertically down and up for patient loading/unloading and for positioning the patient at a height (e.g., iso-center 118) for scanning A vertical drive system (VDS) 120 includes a vertical controller (VC) 122, which drives a vertical motor (VM) 124 that drives the mechanism that raises and lowers the base 114.

The subject support 112 also includes a tabletop 116, which is moveably affixed to the base 114 and configured to move horizontally in/out of the examination region 106 before, during and after scanning. When extended into the examination region, the tabletop 116 cantilevers over the base 114, as shown in dotted line in FIG. 2. A horizontal drive system (HDS) 126 includes a horizontal controller (HC) 128, which drives a horizontal motor (HM) 130 that drives the mechanism that moves the tabletop 116.

In the illustrated embodiment, the subject support 112 also includes a support frame 132. However, it is to be understood that the support frame 132 may be a separate component with the subject support 112 attached thereto, forming a subject support assembly 133. The support frame 132 is configured to be mounted to an examination room floor and allows the base 114 (and thus a relative stationary tabletop 116) to move towards and away from the stationary gantry 102. A support frame drive system (SI-DS) 134 includes a support frame controller (SFC) 136, which drives a support frame motor (SFM) 138 that drives the mechanism that moves the base 114.

In one instance, the movement of the base 114 via the support frame 132 is defined by one or more positioning algorithms 140 stored in storage 142. In the illustrated embodiment, the one or more positioning algorithms 140 cause the base 114 to move through at least two (e.g., two, three, four, etc.) different predetermined locations with respect to the stationary gantry 102. For example, one predetermined algorithm causes the base 114 to move to a trauma location in which the base 114 is separated from the stationary gantry 102, for example, so that trauma equipment can fit between the stationary gantry 102 and the base 114 and/or based on other criteria. At this location, for example, the base 114 may be approximately 350, 500, 625, etc. millimeters away from the stationary gantry 102.

Another predetermined algorithm causes the base 114 to move to a cardiac location in which the base 114 is separated from the stationary gantry 102, for example, so as to reduce the amount of bounce and deflection and increase stiffness of the cantilevering tabletop 116 and/or based on other criteria. At this location, for example, the base 114 may be approximately 50, 94, 120, etc. millimeters away from the stationary gantry 102. Another predetermined algorithm causes the base 114 to move to a general location at which the base 114 is separated from the stationary gantry 102, for example, to provide a minimum predetermined scannable range (e.g., for a full body scan) while also providing access between the stationary gantry 102 and the subject support 112 and/or based on other criteria. At this location, for example, the base 114 may be approximately 200, 280, 350, etc. millimeters away from the stationary gantry 102.

The support frame controller 136 executes a selected one of the one or more positioning algorithms 140 based on a signal from an activation device 144. The device 144 can be located at the stationary gantry 102 (e.g., on the front cover as shown in FIG. 1, on the side as shown in FIG. 2, and/or elsewhere), the subject support 112 (on the back of the tabletop 116 as shown in FIG. 1, on a front side of the tabletop 116, and/or elsewhere, including on the base 114), on the examination room wall, in connection with another device, in a visual display as a software generated graphical indicia or icon, and/or other elsewhere.

More particularly, the activation device 144 includes a physical and/or software generated control 145 such as a button, switch, etc. for each of the positioning algorithms 140 that respectively invoke the corresponding positioning algorithms 140. For example, where the algorithms 140 include three (3) positioning algorithms, each corresponding to a different predetermined (e.g., default and/or user specified) location, the activation device 144 may include three (3) different physical controls 145, one for each of the three algorithms 140. The support frame controller 136 may also be used to place the subject support 112 in a free float mode where an operator can manually move the base 114 to a location of interest.

A reconstructor 146 reconstructs the signal generated by the detector array 110 and generates volumetric image data indicative of the examination region 106. A general purpose computing system serves as the operator console 148, and includes an output device such as a display, an input device such as a keyboard, mouse, and/or the like, one or more processor and computer readable storage medium. The console 148 allows the operator to control operation of the system 100, for example, by displaying a software generated user selectable control in a graphical user interface (GUI) which, when activated, invokes one of the one or more positioning algorithms 140 to cause the base 114 to move to a predetermined location, or through selection of an imaging protocol.

In one non-limiting instance, with the system of FIGS. 1 and 2, at least three of the algorithms 140 may respectively correspond to cardiac, general, and trauma locations of the base 114 with respect to the stationary gantry 102. In this instance, regardless of whether the imaging system 100 is located at a cardiac center, a general imaging center or a trauma center, the imaging system 100 is well-suited for scanning cardiac, general, and trauma a same and/or different subjects.

For example, if a trauma patient arrives, the algorithm 140 for trauma mode can be invoked by activating a corresponding control 145 of the activation device 144 which will move the base 114 to a trauma location. If a cardiac scan and/or general scan are subsequently ordered, for the same or different patient, either cardiac mode or general imaging mode (or one following the other) are invoked by activating the corresponding control of the activation device 144, which will move the base 114 to a cardiac or general location. If another trauma scan is ordered, the trauma location control 145 can be activated again to move the base 114 back to the trauma location.

One or more of the algorithms 140 may also correspond to a service, a calibration, de-installation, etc. mode. However, unlike the trauma, general, cardiac, and/or other patient scanning modes, the service, calibration, de-installation, etc. modes may position the base 114 at a location at which the tabletop 116 is unable to position the object or subject in the examination region 106 for scanning.

Figure 3:
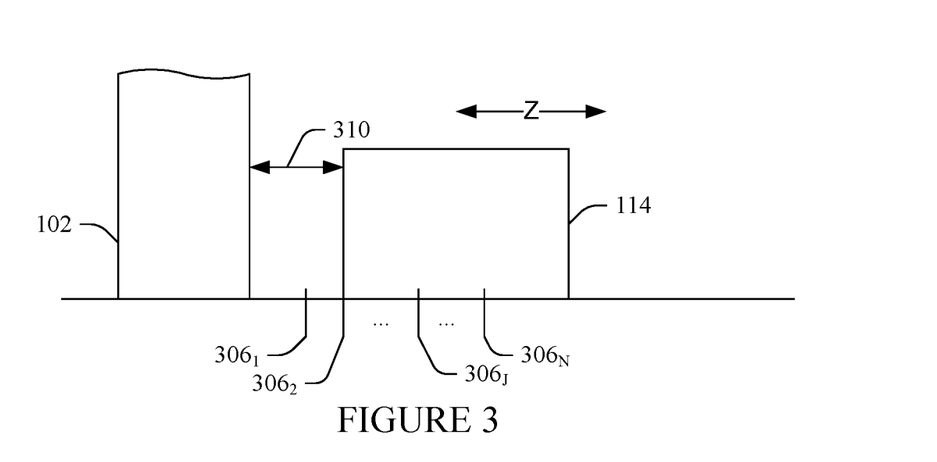
FIGS. 3, 4 and 5 show movement of the base of FIGS. 1 and 2 between three different predetermined locations.
Figure 4:
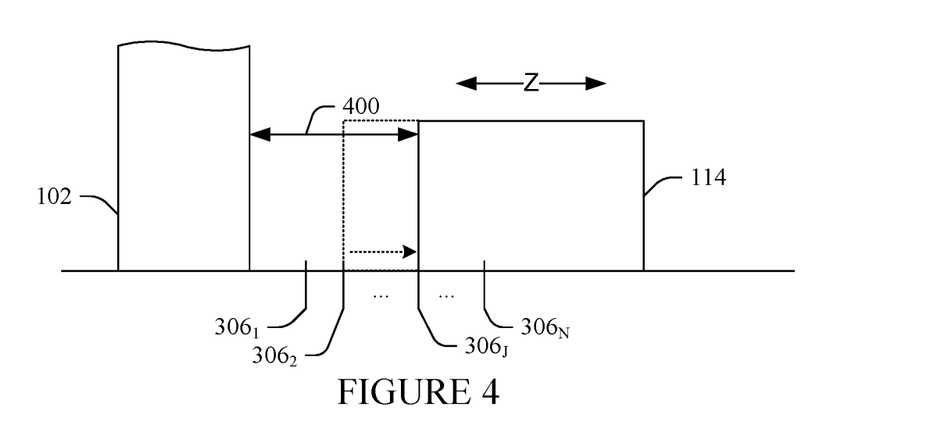
Figure 5:
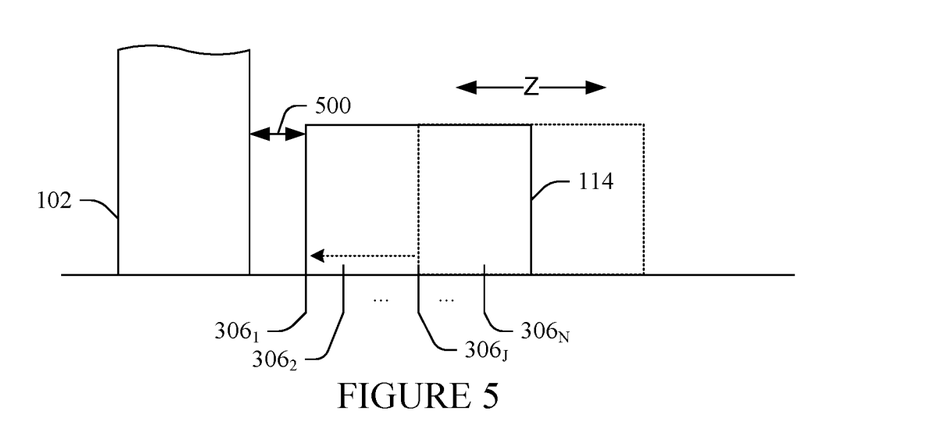

FIGS. 3, 4 and 5 show an example of locations of the base 114 with respect to the stationary gantry 102 based on the positioning algorithms 140. The stationary gantry 102 is located at a fixed position. In this example, the one or more positioning algorithms 140 provide instructions to translate the base 114 alternatively to one of N locations, $306_1$, $306_2$, ..., $306_J$, $306_N$ (where N is an integer), collectively referred to herein as locations 306. Each of the N locations 306 represents a pre-determined distance from the stationary gantry 102 and/or other reference point.

In FIG. 3, the base 114 is located at $306_2$ at a distance 310 from the stationary gantry 102. FIG. 4 shows the base 114 after invoking the corresponding control 145 of the activation device 144 to move the base 114 to the location $306_J$, which places the base 114 at a distance 400 away from the stationary gantry 102. FIG. 5 shows the base 114 after invoking the corresponding control 145 of the activation device 144 to move the base 114 to the location $306_1$ which places the base 114 a distance 500 away from the stationary gantry 102.

Figures 6, 7:
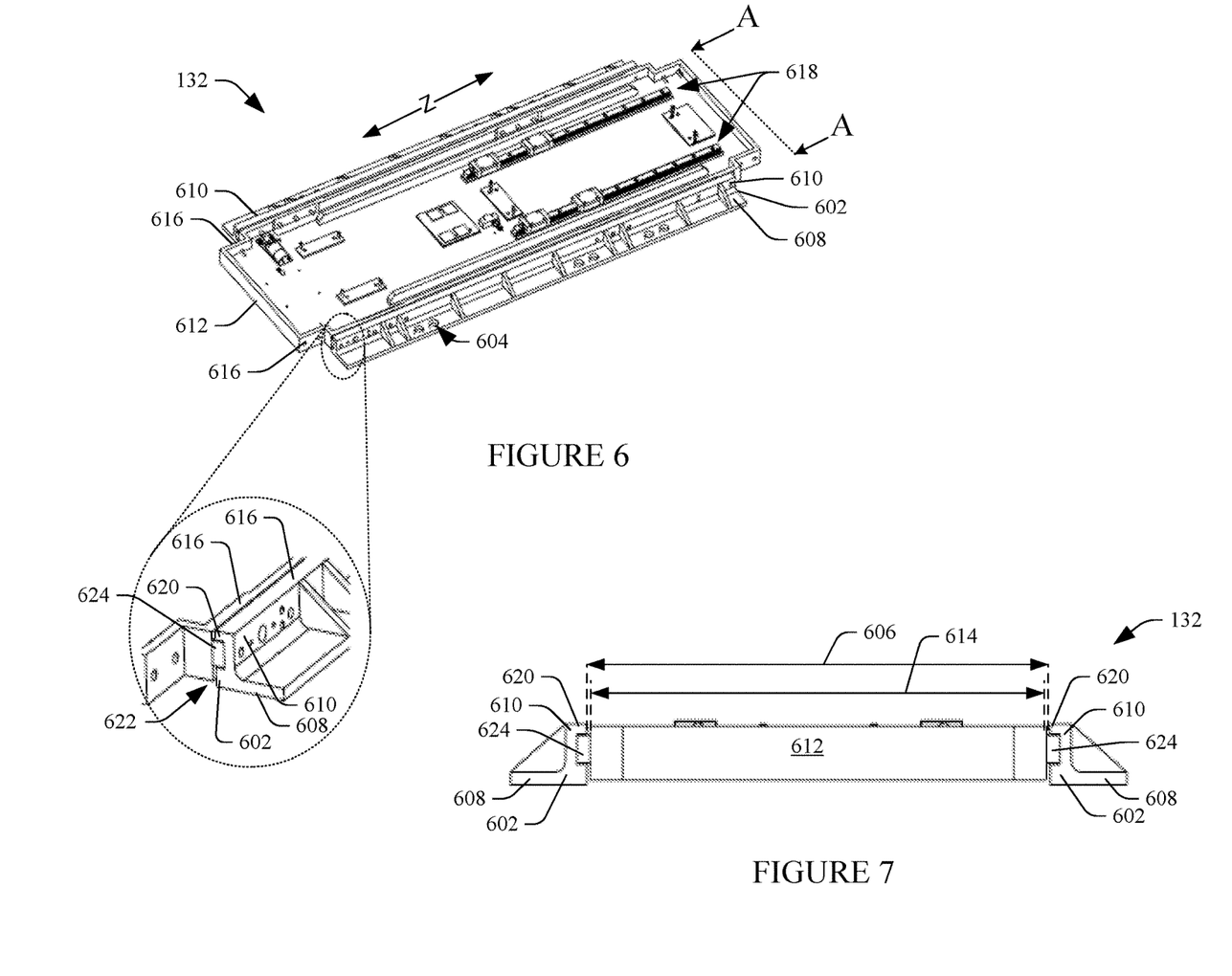
FIGS. 6 and 7 show a non-limiting example of the support frame.

FIGS. 6 and 7 illustrate a non-limiting example of the support frame 132 and the subject support 112. FIG. 6 shows a perspective view, and FIG. 7 shows a view along line A-A of FIG. 6.

In this example, the support frame 132 includes at least one bracket 602 (two are shown in the embodiment of FIGS. 6 and 7) that mounts to the examination room floor. In this embodiment, the at least one bracket 602 includes material free regions 604 through which fasteners (not shown) such as screws, bolts, or the like can be inserted into to fasten to the floor thereby fastening the at least one bracket 602 to the floor.

Each of the illustrated brackets 602 are elongate and orientated, separated apart by a distance 606, such that their long axis runs parallel to the z-axis. In this embodiment, each bracket 602 is "L" shaped with a first leg 608 of the "L" facing and mounted to the floor and a second leg 610 of the "L" facing the second leg 610 of the "L" of the other bracket 602, with the second legs 610 spatially between the first legs 608.

The support frame 132 also includes a moveable cradle 612 that has a geometry in which a width 614 of the moveable cradle 612 is less than the distance 606. Sides 616 of the moveable cradle extend upward in a same direction as the second legs 610 extend. The moveable cradle 612 also includes a fastening assembly 618 for fastening the mechanism that raises and lowers the base 114 to the moveable cradle 612. The moveable cradle 612 may also include fasteners for other devices such as the vertical motor 124, etc.

A first part 620 of a bearing 622 is part of each of the second legs 610 on a side of the second legs 610 facing each other. A second part 624 of the bearing 622 is attached to the moveable cradle sides 616. The first and second parts 620 and 624 are complementary parts of the bearing 622. In the illustrated embodiment, the bearing 622 is a linear slide bearing, the first part 620 includes a generally "C" shaped rail, and the second part 624 includes an elongate member the slides through the "C" shaped rail.

With this embodiment, the base 114 is fastened to the moveable cradle 612, for example, via the fastening assembly 618 and/or otherwise. To position the base 114 based on the positioning algorithms 140, the support frame controller 136, drives the support frame motor 138 to slide the moveable cradle 612 via the bearing 622. An encoder or other device can be used to determine the relative position of the base 114 with respect to the stationary gantry 102.

It is to be appreciated that the support frame 132 can be installed with the subject support 112 at the time of installing the subject support 112 or as an add-on feature to an already installed subject support 112. In the latter case, the subject support 112 would be un-mounted from the examination floor and then fastened to the support frame 132, which would be mounted to the examination room floor.

Figure 8:
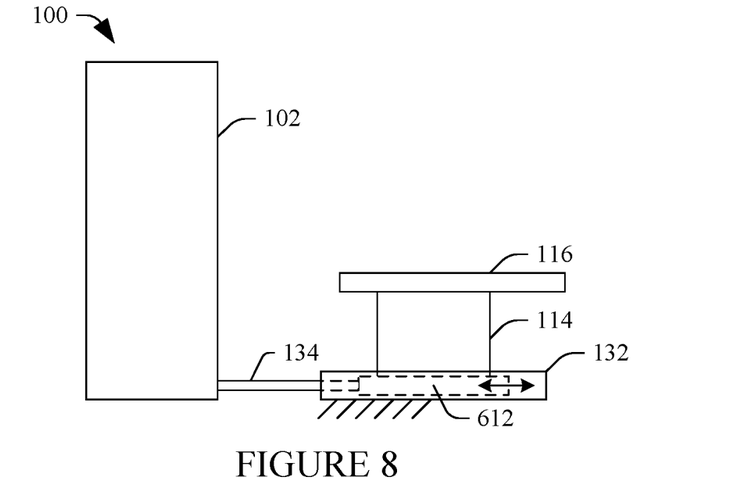
FIGS. 8 and 9 show example locations of the support frame drive system in connection with the support frame of FIGS. 6 and 7.
Figure 9:
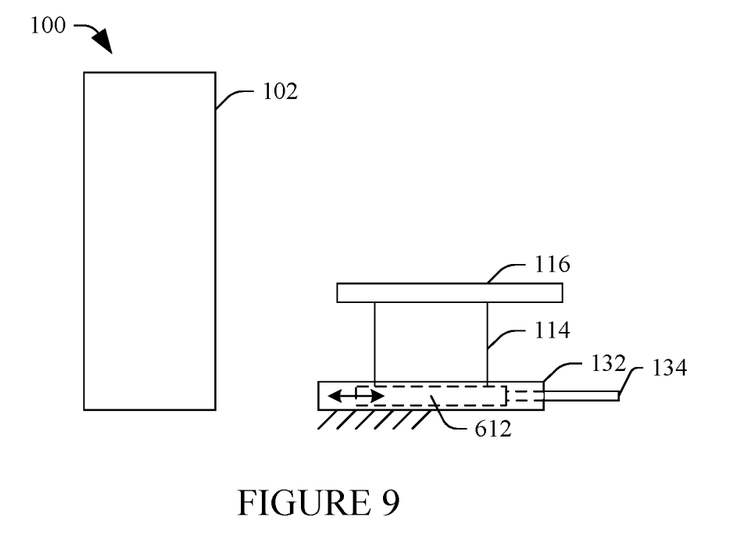

FIGS. 8 and 9 illustrate example locations for the support frame drive system 134 in connection with FIGS. 6 and 7.

In FIG. 8, the support drive system 134 is located between the stationary gantry 102 and the moveable cradle 612 and exerts a force on the moveable cradle 612 to move the moveable cradle 612 and hence the base 114 and tabletop 116 away from the stationary gantry 102, and pulls the moveable cradle 612 to move the moveable cradle 612 and hence the base 114 and tabletop 116 towards the stationary gantry 102.

In FIG. 9, the support drive system 134 is located behind the moveable cradle 612 and exerts a force on the moveable cradle 612 to move the moveable cradle 612 and hence the base 114 and tabletop 116 towards the stationary gantry 102, and pulls the moveable cradle 612 to move the moveable cradle 612 and hence the base 114 and tabletop 116 away from the stationary gantry 102.

Other locations for the support frame drive system 134 are also contemplated herein.

Figure 10:
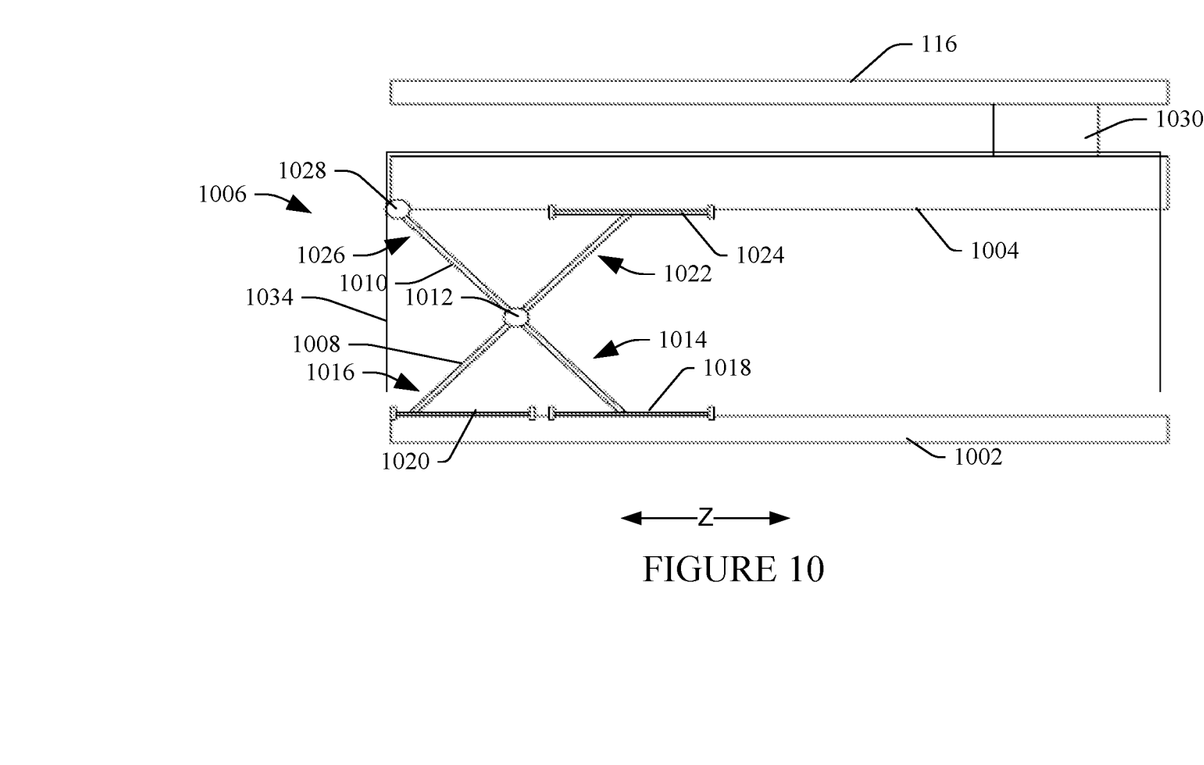
FIG. 10 shows another non-limiting example of the support frame.

FIG. 10 illustrates another non-limiting example of the support frame 132 and the subject support 112. In this example, the base 114 and the support frame 132 are part of a single apparatus. A bottom plate 1002 fixedly attaches to the examination room floor. A top frame 1004 attaches to the bottom plate 1002, through a vertical drive mechanism 1006. In this embodiment, the mechanism 1006 includes a "scissors" like mechanism that includes to first and second elongate members 1008 and 1010 coupled together at a pivot point 1012.

First ends 1014 and 1016 of the members 1008 and 1010 are pivotally and slideably attached respectively to bearings 1018 and 1020, which are affixed to the base plate 1002, and which allow the first ends 1014 and 1016 to pivot and/or to slide in a direction of the z-axis. A second end 1022 of the first member 1008 is likewise pivotally and slideably attached to a bearing 1024 that is affixed to the top frame 1004 and which allows the second end 1022 to pivot and to slide in a direction of the z-axis.

A second end 1026 of the second member 1010 is pivotally attached to the top frame 1004 at a pivot point 1028, which allows the second end 1026 to pivot. The tabletop 116 of the subject support 112 is slideably mounted to the top frame 1104 through a bearing 1030. A cover or shroud 1034 covers the space between the top frame 1004 and the bottom plate 1002. In the illustrated embodiment, the cover 1034 fastens to the top frame 1004.

To move the tabletop 116 vertically up, the vertical drive mechanism 1006 is actuated to move the first ends 1014 and 1016 towards each other (or the second end 1022 towards the second end 1026), which causes the second end 1022 to move towards the second end 1026 (or the first ends 1014 and 1016 towards each other). This results in the elongate members 1008 and 1010 moving to a more vertical position, which raises the top frame 1102 and hence the tabletop 116.

To move the tabletop 116 down, the vertical drive mechanism 1006 is actuated to move the first ends 1014 and 1016 away from each other (or the second end 1022 away from the second end 1026), which causes the second end 1022 to move away from the second end 1026 (or the first ends 1014 and 1016 away from each other). This results in the elongate members 1008 and 1010 moving to a more horizontal position, which lowers the top frame 1102 and hence the tabletop 116.

To move the tabletop 116 horizontally relative to the top frame 1004 and the base 114, the horizontal drive system 126 drives a horizontal motor 130.

To move the top frame 1004 together with the tabletop 116 horizontally towards the stationary gantry 102 based on one of the positioning algorithms 140, the support frame controller 136, drives the support frame motor 138 to slide the entire mechanism 1006, via the exerting a force on the mechanism 1006, the shroud 1034, and/or other component to move the mechanism 1006 along the bearing 1018 and 1020, which moves the top frame 1004 together with the tabletop 116.

To move the top frame 1004 together with the tabletop 116 horizontally away from the stationary gantry 102 based on one of the positioning algorithms 140, the support frame controller 136, drives the support frame motor 138 to slide the mechanism 1006, via the pulling on the mechanism 1006, the shroud 1034, and/or other component to move the mechanism 1006 along the bearing 1018 and 1020, which moves the top frame 1004 together with the tabletop 116. Note that in this embodiment, the bearings 1018 and 1020 are shared by two different systems, the top frame 1004 vertical and the base 114 horizontal systems. This may reduce cost and space requirements relative to a configuration in which different bearings are used for the top frame vertical and horizontal drives systems. In another embodiment, separate bearings can be used.

Figure 11:
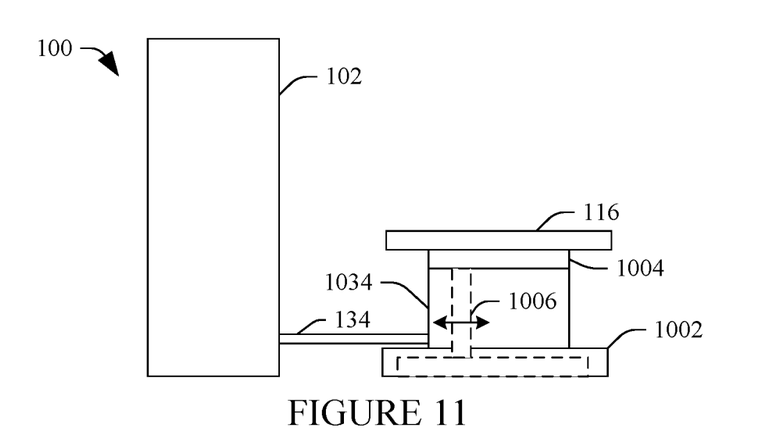
FIGS. 11, 12 and 13 show example locations of the support frame drive system in connection with the support frame of FIG. 10.
Figure 12:
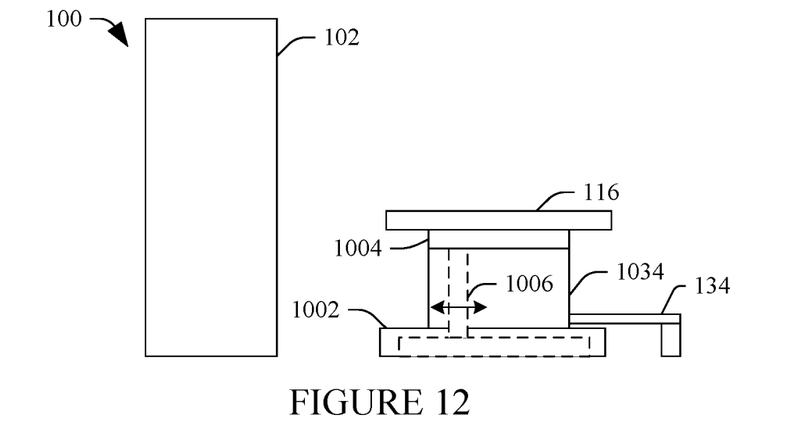
Figure 13:
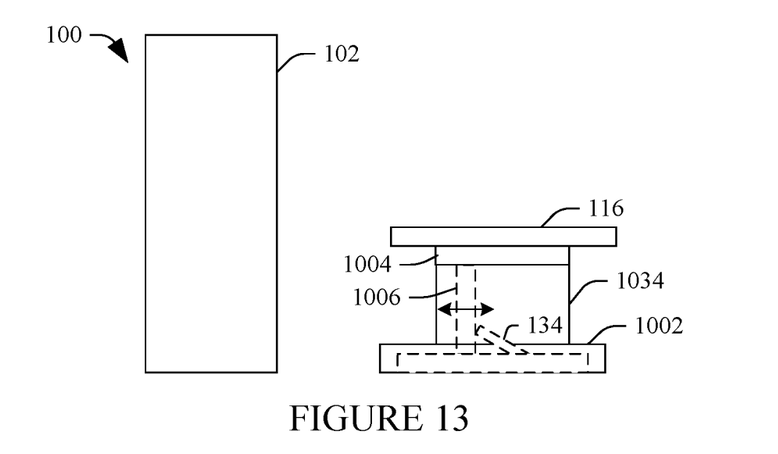

FIGS. 11, 12 and 13 illustrate example locations for the support frame drive system 134 in connection with FIG. 10

In FIG. 11, the support drive system 134 is located between the stationary gantry 102 and the vertical drive mechanism 1006 and exerts a force on the shroud 1034, the mechanism 1006, and/or other component to move the mechanism 1006 and hence the top frame 1004 and tabletop 116 away from the stationary gantry 102, and pulls the shroud 1034, the mechanism 1006, and/or other component to move the mechanism 1006 and hence the top frame 1004 and tabletop 116 towards the stationary gantry 102.

In FIG. 12, the support drive system 134 is located behind the subject support 112 and exerts a force on the shroud 1034, the mechanism 1006, and/or other component to move the mechanism 1006 and hence the top frame 1004 and tabletop 116 towards the stationary gantry 102, and pulls the shroud 1034, the mechanism 1006, and/or other component to move the mechanism 1006 and hence the top frame 1004 and tabletop 116 away from the stationary gantry 102.

In FIG. 13, the support drive system 134 is located inside of the shroud 1034 and affixed to the base plate 1002. In this embodiment, the support drive system 134 is located behind the mechanism 1006, and operates similar to that described in connection with FIG. 12. In a variation, the support drive system 134 is located inside of the base plate 1002 but between the stationary gantry 102 and the mechanism 1006, and operates similar to that described in connection with FIG. 11.

Other locations for the support drive system 134 are also contemplated herein.

Figure 14:
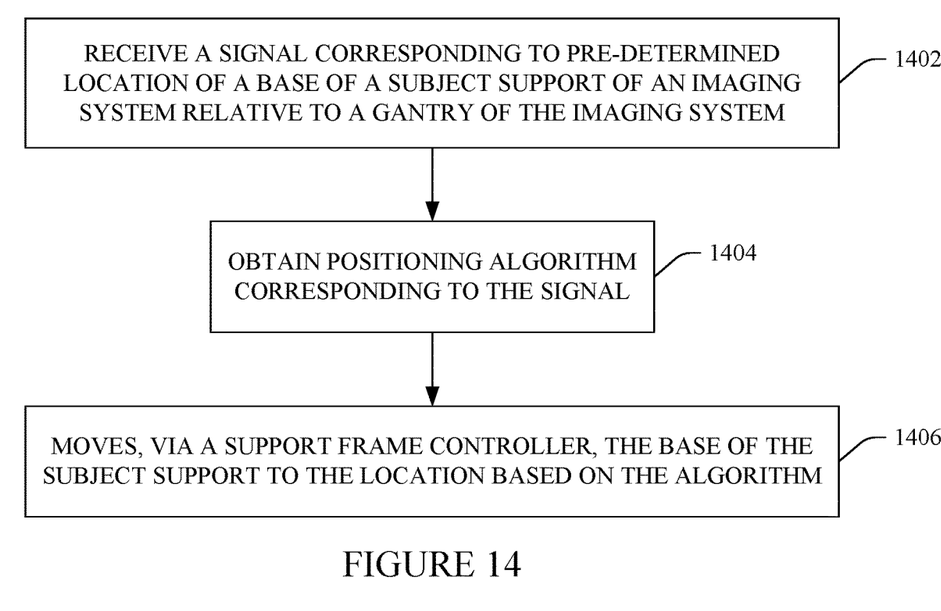
FIGS. 14 and 15 illustrate example methods.

FIG. 14 illustrates an example method in accordance with the embodiments described herein.

At 1402, a signal corresponding to one of a plurality of pre-determined locations for a base of a subject support with respect to a stationary gantry of an imaging system for scanning an object or subject is received.

At 1404, a positioning algorithm corresponding to the signal is obtained.

At 1406, a support frame controller automatically positions the base, via electronic control, based on the obtained algorithm.

Figure 15:
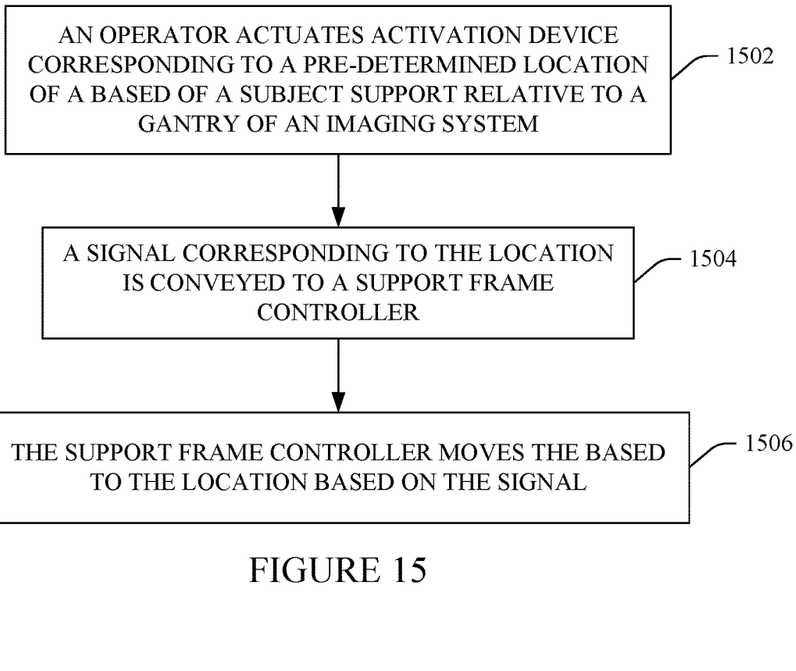

FIG. 15 illustrates an example method in accordance with the embodiments described herein.

At 1502, an operator of an imaging system actuates one of a plurality of controls of an activation device that corresponds to a pre-determined location of interest of a base of a subject support, with respect to a stationary gantry of the imaging system, for scanning an object or subject.

At 1504, in response thereto, a signal indicating the pre-determined position is conveyed to a support frame controller.

At 1506, the support frame controller automatically positions the base at the pre-determined location based on the signal.

It is to be appreciated that the ordering of the acts in the methods described herein is not limiting. As such, other orderings are contemplated herein. In addition, one or more acts may be omitted and/or one or more additional acts may be included.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:
1. A method, comprising:
  receiving a first signal indicating a first preprogrammed horizontal location of a base of a subject support of an imaging system with respect to a gantry of the imaging system, wherein the first preprogrammed horizontal location is one of a plurality of preprogrammed scanning locations, each corresponding to a different predetermined distance between the base and the gantry; and moving, via electronic control, the base to the first location for a first type of scan.

2. The method of claim 1, wherein the first type of scan is a type from a group consisting of a trauma type, a general type and a cardiac type.

3. The method of claim 2, further comprising:

after scanning an object or subject with the subject support at the first preprogrammed horizontal location, receiving a second signal indicative of a second preprogrammed horizontal location of the base, wherein the second preprogrammed horizontal location is one of the plurality of preprogrammed scanning locations; and moving, via the electronic control, the base to the second location for a second type of scan.

4. The method of claim 3, wherein the second type of scan from the group consisting of the trauma type, the general type and the cardiac type.

5. The method of claim 3, wherein the first and the second types of scans are scans of a same imaging modality.

6. The method of claim 2, further comprising:

positioning a tabletop supported by the base at a same examination region for each of the trauma type, the general type and the cardiac type of scans.

7. The method of claim 2, further comprising:

moving the base to a distance of 350 to 625 millimeters for a trauma type of scan, 200 to 350 millimeters for a general type of scan, and 50 to 120 millimeters for a cardiac type of scan.

8. The method of claim 1, wherein moving the base includes moving an entirety of the base tabletop along brackets disposed on an examination room floor.

9. The method of claim 1, wherein the different predetermined distances are from a front of the base to the gantry, where the front of the base is a portion of the base closest to the gantry.

10. An imaging system, comprising:

a gantry that defines an examination region; and a subject support, including:
  a tabletop;
  a base that supports the tabletop:
  a support frame/bottom plate;
  a cover that covers the support frame/bottom plate and a space between the support frame/bottom plate and the base; and
  a horizontal drive system configured to move the base to one of a plurality of predetermined locations in response to an input signal indicative of the one of the plurality of predetermined locations, which corresponds to a location of interest for the scan of an object or subject, by exerting a force on the cover.

11. The imaging system of claim 10, wherein the horizontal drive system pushes or pulls the cover to move the base.

12. The imaging system of claim 10, wherein the horizontal drive system is disposed between the gantry and the subject support.

13. The imaging system of claim 10, wherein the subject support is disposed between the gantry and the horizontal drive system.

14. The imaging system of claim 10, wherein the support frame/bottom plate includes first and second bearings, and the base includes:

a top frame with a third bearing; and a vertical drive coupled between the top frame and the support frame/bottom plate, wherein the vertical drive includes first and second elongate members, which are coupled together at a central region at a pivot point, wherein a first end of the first elongate member is pivotally and slideably attached to the first bearing, a second end of the second elongate member is pivotally and slideably attached to the second bearing, a third end of the second elongate member is pivotally and slideably attached to the third bearing and a fourth end of the first elongate member is fixedly attached to the top frame; and wherein the support frame/base plate supports the base the vertical drive of the base is moveably affixed to the support frame/base plate through the first and second bearings, the base movable between a plurality of predetermined locations, which are based on corresponding distances from the gantry.

15. A computer readable storage medium encoded with computer readable instructions, which, when executed by a processor, cause the processor to:

receive a first signal indicating a first preprogrammed distance between a front of a base of a subject support of an imaging system and a gantry of the imaging system, wherein the first preprogrammed distance is a distance from a group consisting of a distance for a trauma scan, a distance for a general scan and a distance for a cardiac scan, wherein the distance for the trauma scan, the distance for the general scan and the distance for the cardiac scan are different distances; and move the base to a first location corresponding to the first preprogrammed distance.

16. The computer readable storage medium of claim 15, wherein the computer readable instructions, when executed by a processor, further cause the processor to:

receive a second signal indicating a second preprogrammed distance between the front and the gantry, wherein the second preprogrammed distance is a distance from the group consisting of the distance for the trauma scan, the distance for the general scan and the distance for the cardiac scan; and move the base to a second location corresponding to the second preprogrammed distance.

17. The computer readable storage medium of claim 16, wherein the first location corresponds to a first type of scan, the second location corresponds to a second type of scan, and the first and second types of scan are different types of scans.

18. The computer readable storage medium of claim 15, wherein the computer readable instructions, when executed by a processor, further cause the processor to:

move the base via a moveable cradle slidably attached to bearings mounted to an examination room floor.

19. The computer readable storage medium of claim 15, wherein the computer readable instructions, when executed by a processor, further cause the processor to:

control a horizontal drive system to push or pull on a cover of the subject support to move the base.

* * * * *